US011185613B2

United States Patent
Montes de Oca Balderas et al.

(10) Patent No.: US 11,185,613 B2
(45) Date of Patent: Nov. 30, 2021

(54) SELECTIVELY WATER DISINTEGRABLE MATERIALS AND CATHETERS MADE OF SUCH MATERIALS

(71) Applicant: Hollister incorporated, Libertyville, IL (US)

(72) Inventors: Horacio Montes de Oca Balderas, Ballina (IE); John T. Clarke, Galway (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 15/736,685

(22) PCT Filed: Jun. 15, 2016

(86) PCT No.: PCT/US2016/037650
§ 371 (c)(1),
(2) Date: Dec. 14, 2017

(87) PCT Pub. No.: WO2016/205383
PCT Pub. Date: Dec. 22, 2016

(65) Prior Publication Data
US 2018/0185551 A1 Jul. 5, 2018

Related U.S. Application Data

(60) Provisional application No. 62/181,056, filed on Jun. 17, 2015.

(51) Int. Cl.
*A61L 29/04* (2006.01)
*A61L 29/14* (2006.01)
(Continued)

(52) U.S. Cl.
CPC .......... *A61L 29/049* (2013.01); *A61L 29/085* (2013.01); *A61L 29/141* (2013.01); *A61L 2420/06* (2013.01)

(58) Field of Classification Search
CPC .. A61L 29/049; A61L 29/085; A61L 2420/06; C08L 29/04; A61M 25/0043; A61M 25/0048
See application file for complete search history.

(56) References Cited

U.S. PATENT DOCUMENTS 3,583,391 A    6/1971   Cox et al.
3,621,848 A   11/1971   Magovern
(Continued)

FOREIGN PATENT DOCUMENTS

CN           2240371      11/1996
CN    101300036 A    11/2008
(Continued)

OTHER PUBLICATIONS

International Preliminary Report on Patentability for International application No. PCT/US2016/037650 dated Dec. 19, 2017.
(Continued)

*Primary Examiner* — Joanna Pleszczynska
(74) *Attorney, Agent, or Firm* — Cook Alex Ltd.

(57) ABSTRACT

Polymeric materials that are blends of polymers having differing water solubility rates are disclosed. The blends may be incorporated into at least a portion of a medical devices such as the shafts of flushable urinary catheters to provide suitable catheter stiffness/flexibility and catheter disintegration in water receptacles such as toilets. The blended material may provide the substrate of the catheter shaft or may provide one or more layers of the catheter.

7 Claims, 1 Drawing Sheet

(51) Int. Cl.
*A61M 25/00* (2006.01)
*C08L 29/04* (2006.01)
*A61L 29/08* (2006.01)

(56) References Cited

U.S. PATENT DOCUMENTS

| | | | |
|---|---|---|---|
| 3,702,610 A | 11/1972 | Sheppard et al. | |
| 3,861,396 A | 1/1975 | Vaillancourt et al. | |
| 3,894,540 A | 7/1975 | Bonner, Jr. | |
| 4,062,363 A | 12/1977 | Bonner, Jr. | |
| 4,100,309 A | 7/1978 | Micklus et al. | |
| 4,155,971 A * | 5/1979 | Wysong | C08L 29/04 264/204 |
| 4,227,533 A | 10/1980 | Godfrey | |
| 4,413,986 A | 11/1983 | Jacobs | |
| 4,416,791 A * | 11/1983 | Haq | C11D 17/042 510/296 |
| 4,465,481 A | 8/1984 | Blake | |
| 4,594,407 A | 6/1986 | Nyilas et al. | |
| 4,610,671 A | 9/1986 | Luther | |
| 4,668,221 A | 5/1987 | Luther | |
| 4,762,738 A | 8/1988 | Keyes et al. | |
| 4,769,005 A | 9/1988 | Ginsburg et al. | |
| 4,772,279 A | 9/1988 | Brooks et al. | |
| 4,790,817 A | 12/1988 | Luther | |
| 4,790,831 A | 12/1988 | Skribiski | |
| 4,795,439 A | 1/1989 | Guest | |
| 4,840,622 A | 6/1989 | Hardy | |
| 4,849,256 A * | 7/1989 | Newman | C08J 3/124 427/202 |
| 4,883,699 A | 11/1989 | Aniuk et al. | |
| 4,906,238 A | 3/1990 | Greenfeld et al. | |
| 4,952,359 A | 8/1990 | Wells | |
| 4,954,129 A | 9/1990 | Giuliani et al. | |
| 4,994,047 A | 2/1991 | Walker et al. | |
| 5,002,526 A | 3/1991 | Herring | |
| 5,009,648 A | 4/1991 | Aronoff et al. | |
| 5,089,535 A | 2/1992 | Malwitz et al. | |
| 5,098,535 A | 3/1992 | Nakakoshi et al. | |
| 5,102,401 A | 4/1992 | Lambert et al. | |
| 5,108,382 A | 4/1992 | Wright et al. | |
| 5,195,962 A | 3/1993 | Martin et al. | |
| 5,270,086 A | 12/1993 | Hamlin | |
| 5,439,454 A | 8/1995 | Lo et al. | |
| 5,468,526 A | 11/1995 | Allen et al. | |
| 5,472,417 A | 12/1995 | Martin et al. | |
| 5,569,219 A | 10/1996 | Hakki et al. | |
| 5,601,538 A | 2/1997 | Deem | |
| 5,616,126 A | 4/1997 | Malekmehr et al. | |
| 5,688,459 A | 11/1997 | Mao et al. | |
| 5,776,611 A | 7/1998 | Elton et al. | |
| 5,792,114 A | 8/1998 | Fiore | |
| 5,800,412 A | 9/1998 | Zhang et al. | |
| 5,804,653 A | 9/1998 | Weng | |
| 5,904,703 A | 5/1999 | Gilson | |
| 5,985,394 A | 11/1999 | Mao et al. | |
| 6,017,334 A | 1/2000 | Rawls | |
| 6,030,369 A | 2/2000 | Engelson et al. | |
| 6,063,063 A | 5/2000 | Harboe et al. | |
| 6,066,120 A | 5/2000 | Whiteside | |
| 6,071,618 A | 6/2000 | Cook, Jr. et al. | |
| 6,090,075 A | 7/2000 | House | |
| 6,213,990 B1 | 4/2001 | Roempke | |
| 6,217,569 B1 | 4/2001 | Fiore | |
| 6,447,835 B1 | 9/2002 | Wang et al. | |
| 6,468,245 B2 | 10/2002 | Alexandersen | |
| 6,471,684 B2 | 10/2002 | Dulak et al. | |
| 6,488,659 B1 | 12/2002 | Rosenman | |
| 6,585,721 B2 | 7/2003 | Fiore | |
| 6,627,586 B1 | 9/2003 | Brooks et al. | |
| 6,656,146 B1 | 12/2003 | Clayman et al. | |
| 6,664,333 B2 | 12/2003 | Wang et al. | |
| 6,713,140 B2 | 3/2004 | McCormack et al. | |
| 6,726,654 B2 | 4/2004 | Rosenman | |
| 6,942,635 B2 | 9/2005 | Rosenblatt et al. | |
| 6,960,224 B2 | 11/2005 | Marino et al. | |
| 6,976,973 B1 | 12/2005 | Ruddell et al. | |
| 7,037,295 B2 | 5/2006 | Tiernan et al. | |
| 7,112,298 B2 * | 9/2006 | Kampa | A61L 29/085 264/301 |
| 7,128,862 B2 | 10/2006 | Wang | |
| 7,156,824 B2 | 1/2007 | Rosenman | |
| 7,182,906 B2 | 2/2007 | Chen | |
| 7,402,620 B2 | 7/2008 | McGhee | |
| 7,553,923 B2 | 6/2009 | Williams | |
| 7,601,158 B2 | 10/2009 | House | |
| 7,641,757 B2 | 1/2010 | Kampa et al. | |
| 7,662,146 B2 | 2/2010 | House | |
| 7,731,740 B2 | 6/2010 | LaFont et al. | |
| 7,789,873 B2 | 9/2010 | Kubalak et al. | |
| 7,815,628 B2 | 10/2010 | Devens, Jr. | |
| 7,820,284 B2 | 10/2010 | Terry | |
| 7,824,517 B2 | 11/2010 | Kampa et al. | |
| 7,833,280 B2 | 11/2010 | Stack et al. | |
| 7,947,031 B2 | 5/2011 | DiMatteo et al. | |
| 8,143,368 B2 | 3/2012 | Domb et al. | |
| 8,168,249 B2 | 5/2012 | Utas et al. | |
| 8,187,254 B2 | 5/2012 | Hissink | |
| 8,241,656 B2 | 8/2012 | Chudzik et al. | |
| 8,287,890 B2 | 10/2012 | Elton | |
| 8,388,583 B2 | 3/2013 | Stout | |
| 8,388,585 B2 | 3/2013 | Tomes | |
| 8,469,928 B2 | 6/2013 | Stout | |
| 8,518,019 B2 | 8/2013 | Green | |
| 8,569,402 B2 | 10/2013 | Henderson et al. | |
| 8,697,624 B2 * | 4/2014 | Denome | B65D 65/46 510/296 |
| 8,827,984 B2 | 9/2014 | Lovmar et al. | |
| 8,907,155 B2 | 12/2014 | Wang et al. | |
| 2002/0016574 A1 | 2/2002 | Wang et al. | |
| 2003/0165647 A1 | 9/2003 | Kaneko et al. | |
| 2003/0187368 A1 | 10/2003 | Sata et al. | |
| 2003/0228434 A1 | 12/2003 | Bailey et al. | |
| 2004/0122382 A1 | 6/2004 | Johnson et al. | |
| 2004/0210180 A1 | 10/2004 | Altman | |
| 2004/0220550 A1 | 11/2004 | Schryver | |
| 2004/0230177 A1 | 11/2004 | DiMatteo et al. | |
| 2004/0232589 A1 | 11/2004 | Kawabata et al. | |
| 2005/0049577 A1 | 3/2005 | Snell et al. | |
| 2005/0109648 A1 | 5/2005 | Kerzman et al. | |
| 2005/0131386 A1 | 6/2005 | Freeman et al. | |
| 2005/0163844 A1 | 7/2005 | Ashton | |
| 2005/0197627 A1 | 9/2005 | Huang et al. | |
| 2005/0218154 A1 | 10/2005 | Selsby | |
| 2005/0277862 A1 | 12/2005 | Anand | |
| 2005/0283111 A1 | 12/2005 | Maurice | |
| 2006/0173422 A1 | 8/2006 | Reydel et al. | |
| 2006/0240064 A9 | 10/2006 | Hunter et al. | |
| 2006/0276894 A1 | 12/2006 | Finley | |
| 2007/0043333 A1 | 2/2007 | Kampa et al. | |
| 2007/0078412 A1 | 4/2007 | McGuckin, Jr. et al. | |
| 2007/0088330 A1 | 4/2007 | House | |
| 2007/0178299 A1 * | 8/2007 | Verrall | B82Y 30/00 428/323 |
| 2007/0203502 A1 | 8/2007 | Makker et al. | |
| 2007/0225649 A1 | 9/2007 | House | |
| 2008/0015527 A1 | 1/2008 | House | |
| 2008/0091145 A1 | 4/2008 | House | |
| 2008/0097411 A1 | 4/2008 | House | |
| 2008/0118544 A1 | 5/2008 | Wang | |
| 2008/0147049 A1 | 6/2008 | House et al. | |
| 2008/0171991 A1 | 7/2008 | Kourakis | |
| 2008/0171998 A1 | 7/2008 | House | |
| 2008/0172042 A1 | 7/2008 | House | |
| 2008/0183262 A1 | 7/2008 | Dowling | |
| 2008/0194707 A1 | 8/2008 | Potter | |
| 2008/0255510 A1 | 10/2008 | Wang | |
| 2008/0268193 A1 | 10/2008 | Cherry et al. | |
| 2008/0292776 A1 | 11/2008 | Dias et al. | |
| 2008/0312550 A1 | 12/2008 | Nishtala | |
| 2009/0018530 A1 | 1/2009 | Nielsen et al. | |
| 2009/0036874 A1 | 2/2009 | Horowitz et al. | |
| 2009/0250370 A1 | 10/2009 | Whitchurch | |

(56) References Cited

U.S. PATENT DOCUMENTS

| | | | |
|---|---|---|---|
| 2009/0264869 A1* | 10/2009 | Schmid | A61L 29/085 604/544 |
| 2010/0030197 A1 | 2/2010 | House | |
| 2010/0049146 A1 | 2/2010 | Nielsen et al. | |
| 2010/0098746 A1 | 4/2010 | King | |
| 2010/0100116 A1 | 4/2010 | Brister et al. | |
| 2010/0137743 A1 | 6/2010 | Nishtala | |
| 2010/0145315 A1 | 6/2010 | House | |
| 2010/0198195 A1 | 8/2010 | Nishtala et al. | |
| 2010/0204682 A1 | 8/2010 | Tanghoj et al. | |
| 2010/0209472 A1 | 8/2010 | Wang | |
| 2010/0215708 A1 | 8/2010 | Zumbuehl et al. | |
| 2010/0312255 A1 | 12/2010 | Satake et al. | |
| 2010/0323189 A1 | 12/2010 | Illsley et al. | |
| 2011/0049146 A1 | 3/2011 | Illsley et al. | |
| 2011/0071507 A1 | 3/2011 | Svensson et al. | |
| 2011/0114520 A1 | 5/2011 | Matthison-Hansen | |
| 2011/0125135 A1 | 5/2011 | Ahmed | |
| 2011/0160662 A1 | 6/2011 | Stout | |
| 2011/0178425 A1 | 7/2011 | Nishtala | |
| 2011/0212157 A1 | 9/2011 | Edelson et al. | |
| 2011/0238163 A1 | 9/2011 | Andrews et al. | |
| 2011/0268938 A1 | 11/2011 | Schuhmann | |
| 2012/0035530 A1 | 2/2012 | Wang | |
| 2012/0108902 A1* | 5/2012 | Frassica | A61B 1/00082 600/114 |
| 2012/0121919 A1 | 5/2012 | Nielsen | |
| 2012/0296366 A1* | 11/2012 | Rundquist | A61M 25/0029 606/192 |
| 2013/0131646 A1 | 5/2013 | Gilman | |
| 2013/0345681 A1 | 12/2013 | Hong | |
| 2014/0180261 A1 | 6/2014 | Nyman et al. | |

FOREIGN PATENT DOCUMENTS

| | | |
|---|---|---|
| DE | 10 2011 119160 A1 | 5/2013 |
| EP | 0010171 A1 | 4/1980 |
| EP | 0166998 B1 | 1/1986 |
| EP | 0613672 A1 | 9/1994 |
| EP | 0628586 B1 | 12/1994 |
| EP | 0692276 A2 | 1/1996 |
| EP | 1062920 A1 | 12/2000 |
| EP | 1110561 A2 | 6/2001 |
| EP | 1415671 A1 | 5/2004 |
| EP | 2026846 A1 | 2/2009 |
| EP | 2301595 A1 | 3/2011 |
| EP | 2520412 A1 | 11/2012 |
| EP | 2609956 A1 | 7/2013 |
| GB | 1086416 A | 10/1967 |
| GB | 2083762 A | 3/1982 |
| GB | 2496901 A | 5/2013 |
| JP | S-61209655 A | 9/1986 |
| JP | 01-136662 A | 5/1989 |
| JP | 11151293 A | 6/1999 |
| KR | 2000/065291 A | 11/2000 |
| KR | 100754057 B | 8/2007 |
| WO | WO 89/05671 A1 | 6/1989 |
| WO | WO 96/41653 A1 | 12/1996 |
| WO | WO 1998/058989 A1 | 12/1998 |
| WO | WO 00/30696 A1 | 6/2000 |
| WO | WO 2006/055847 A2 | 5/2006 |
| WO | WO 2006/071813 A2 | 7/2006 |
| WO | WO 2007/122269 A1 | 11/2007 |
| WO | WO 2007/140320 A2 | 12/2007 |
| WO | WO 2010/043565 A1 | 4/2010 |
| WO | WO 2011/076211 A1 | 6/2011 |
| WO | WO 2012/163413 A1 | 12/2012 |
| WO | WO 2012/166967 A1 | 12/2012 |
| WO | WO 2014/077886 A1 | 5/2014 |
| WO | WO 2014/193402 A1 | 12/2014 |
| WO | WO2015069843 | 5/2015 |
| WO | WO2015089181 | 6/2015 |
| WO | WO2015089197 | 6/2015 |

OTHER PUBLICATIONS

Rachna N. Dave, Hiren M. Joshi, and Vayalam P. Benugopalan, Novel Biocatalytic Polymer-Based Antimicrobial Coatings as Potential Ureteral Biomaterial, Antimicrobial Agents and Chemotherapy, Feb. 2011, p. 845-853.

Beom Soo Kim, Jeffrey S. Hrkach, Robert Langer, Biodegradable photo-crosslinked poly (ether-ester) networks for lubricious coatings, Biomaterials, vol. 21, Issue 3, Feb. 2000, pp. 259-265.

A.K. Singla, M. Chawla, Chitosan: some pharmaceutical and biological aspects, an update, Journal of Pharmacy and Pharmacology, Aug. 2001, 53: 1047-1067.

FreeStyle Vie Flushable Colostomy Bag by CliniMed Ltd., retrieved from http://www.clinimed.co.uk/Stoma-Care/Products/Closed-Stoma-Bags/Freestyle-Vie-Flushable/Product-Design.aspx Jan. 1, 2014.

International Search Report and Written Opinion for International Application No. PCT/US2014/069508 dated Jun. 10, 2015.

\* cited by examiner

SELECTIVELY WATER DISINTEGRABLE MATERIALS AND CATHETERS MADE OF SUCH MATERIALS

CROSS REFERENCE TO RELATED APPLICATIONS

This application is a National Stage of PCT International Application No. PCT/US2016/037650, filed Jun. 15, 2016 which claims the benefit of and priority to U.S. Provisional Patent Application No. 62/181,056, filed Jun. 17, 2015, the contents of both of which are incorporated herein by reference.

FIELD OF THE DISCLOSURE

The present disclosure is directed to water soluble materials suitable for use in the manufacture of medical devices such as, but not limited to, catheters. More particularly, the present disclosure is directed to polymeric materials that are blends of two or more polymers wherein the polymeric material is selectively water soluble and can act as a suitable substrate for use as a flushable hydrophilic intermittent urinary catheter.

BACKGROUND

Flushable urinary catheter products made from water disintegrable materials are desirable. However, using lubricous hydrophilic coatings with catheters made from water disintegrable materials presents its own challenges. For example, lubricious hydrophilic coatings are activated by water hydration. Because the water disintegrable materials of the catheter breakdown or dissolve in water, the water used to activate the hydrophilic coating may begin breaking down the disintegrable material during such use. This can result in premature weakening of the catheter structure and separation of the hydrophilic coating from the catheter during use. Accordingly, there is a need for a material that can be used to manufacture water disintegrable medical devices such as, but not limited to, urinary catheters wherein (1) the water solubility can be controlled or modulated, (2) the flexibility/stiffness of the catheter is retained during use, and (3) the water disintegrable material provides a suitable and stable substrate for certain hydrophilic coatings that may be applied to the substrate. In addition, there exists a need for flushable catheters with rates of dissolution/disintegration that meet current regulatory or other requirements and, at the same time, balance such rates against the need to maintain at least the minimum mechanical strength of the catheter during catheterization (even where the catheter has already started dissolving.)

SUMMARY

In one aspect, the present disclosure is directed to a polymeric material that is made of a blend of two or more polymers wherein one of the polymers has a first water solubility rate and the other of the two or more polymers has a different water solubility rate.

The polymeric material may be used in the manufacture of medical devices or portions of medical devices, such as medical devices that are insertable into the body of a patient or user including, but not limited to, catheters. Accordingly, in another aspect, the present disclosure is directed to a medical device or a portion of a medical device made of a polymeric material that is a blend of two or more polymers wherein one of the polymers has a first water solubility rate and the other of the two or more polymers has a different solubility rate.

In a more particular aspect the blend may include a cold water soluble polymer and a non-cold water soluble polymer.

In another more particular aspect, the present disclosure is directed to a flushable urinary catheter that includes a shaft at least a portion of which is made of a polymeric material that is a blend of two or more polymers. One of the polymers has a first water solubility rate and the other of the two or more polymers has a different water solubility rate.

DETAILED DESCRIPTION OF THE EMBODIMENTS

Medical devices in accordance with the present disclosure are described below in the context of a urinary catheter. However, it will be appreciated that medical devices other than urinary catheters and/or portions or components of medical devices other than urinary catheters are also contemplated by the present disclosure.

Figure 1:
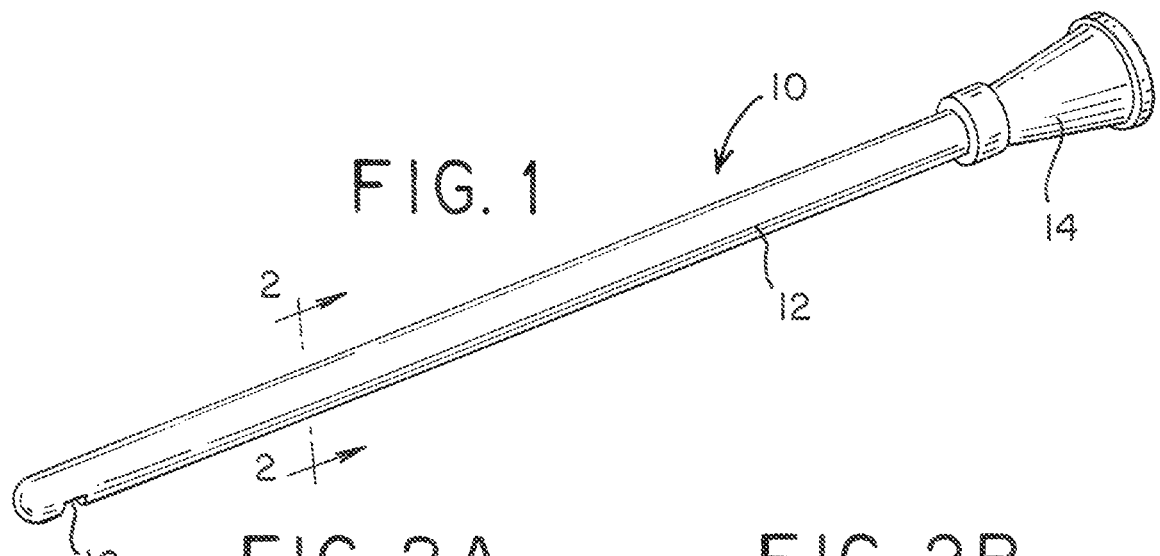
FIG. 1 is a perspective view of a urinary catheter including a catheter tube made of the polymeric materials described herein.

With reference to the Figures, FIG. 1 shows a catheter 10 such as a flushable hydrophilic urinary catheter made at least in part of the polymeric material (blends) disclosed herein. Urinary catheter 10 may be of typical construction and includes catheter tube 12. Funnel 14 of catheter 10 is in flow communication with catheter tube 12. As will be understood by those of skill in the art, tube 12 may include one or more eyelets 16 through which urine enters the internal lumen 18 of catheter tube 12 when catheter 10 is in use (i.e., inserted into the urethra of the patient).

In accordance with the present disclosure, catheter tube 12 and/or funnel 14 may be made, at least in part, of a water disintegrable material of the type disclosed below. In one embodiment, the polymeric material may be a blend of two or more polymers selected to provide a catheter that (1) maintains the necessary stiffness and flexibility during use, (2) is compatible with certain hydrophilic coatings which, when activated, provide a catheter tube 12 with a sufficient amount of lubricity to allow the user to comfortably insert, advance and withdraw catheter tube 12 from the user's urethra and (3) do not degrade too quickly during use and yet are water soluble in accordance with required dissolution rates for disposing of the catheters down the toilet.

In a more particular embodiment, at least a portion of catheter tube 12 and/or funnel 14 may be made of a blend of one or more cold water soluble polymer(s) and one or more non-cold water soluble polymer(s) such as a lukewarm water soluble polymer(s) or a hot water soluble polymer. A "cold water soluble" polymer is generally one wherein a 40 μm thick film of the polymer material at least substantially disintegrates in less than 30 seconds in water at approximately 20° C. A "lukewarm water soluble" material is generally one wherein a 40 μm thick film of the polymer material at least substantially disintegrates in under 40 seconds in water at approximately 55° C. and a "hot water soluble" material is generally one wherein a 40 μm thick film of such polymer material at least substantially disintegrates in under 20 seconds in water at approximately 70° C.

Preferably, cold water soluble and non-cold water soluble polymer(s) that make up the bulk of the blend are of the same general type of polymer that differ at least in the rate at which they disintegrate in water. For example, in one embodiment, the polymers that make up the blend of the polymeric material that is the subject of the present disclosure may be different grades of the same polymer, such as different grades of polyvinyl alcohol (PVOH). In one specific embodiment, the bulk of the blend may be one or more cold water soluble PVOH polymers and one or more non-cold water soluble PVOH polymers. Alternatively, one of the water soluble polymers (cold or non-cold water soluble) may be PVOH while the other water soluble polymer may be a different polymer.

PVOH comes in a variety of grades including cold water soluble PVOH and non-cold water soluble PVOH. For example, Kuraray provides a range of cold water soluble Mowiflex polyvinyl alcohol polymers such as TC 232, TC 251 and TC 253. These water soluble materials can be extruded into tubes for use in the manufacture of flushable urinary intermittent catheters. However, these materials tend to dissolve too quickly at 37° C. and may not have the correct stiffness properties for a urinary catheter. Other PVOH polymers are not cold water soluble. For example, Mowiflex TC 661, also available from Kuraray is not cold water soluble. It is marketed as being lukewarm soluble, i.e. soluble at temperatures above 55° C. and will not readily dissolve after flushing. Similarly, Mowiflex TC 161, also from Kuraray, is advertised as being hot-water soluble, i.e. soluble at temperatures above 70° C.

In accordance with the present disclosure, a blend of TC 661 and/or TC 161 polymer with TC 232, TC 251 and/or TC 253 (cold water soluble PVOH polymers) will result in polymer blends with tailored/modified dissolution rates. For example, blending cold water soluble polymers (e.g., PVOH) with TC 661 and/or TC 161 will slow down the bulk dissolution rates of the cold water soluble polymers when used as a catheter.

In addition to blends of cold water and non-cold water soluble PVOH polymers, the polymeric materials of the present disclosure may further include a plasticizer, the plasticizer also being blended and extruded with the PVOH polymers. One such suitable plasticizer/agent is propylene glycol (PG). Other suitable plasticizers are described in U.S. Pat. No. 2,948,647, the contents of which are incorporated herein by reference. The polymeric materials described herein may be plasticized by exposure to an environment of a selected relative humidity. Plasticization of the materials of the present disclosure by exposure to an environment of a selected relative humidity may be carried out in lieu of or in combination with plasticization by introduction of a suitable plasticizer (such as PG).

In one embodiment, the polymeric material of the present disclosure may include approximately 1-80 wt % of a cold water soluble polymer (such as, but not limited to, PVOH); approximately 1-80 wt % of a non-cold water soluble polymer (such as, but not limited to, PVOH); and approximately 0-35 wt % of a plasticizer. In general, it may be desirable to include a higher concentration of cold water soluble polymer (relative to the non-cold water soluble polymer). In another more specific embodiment, the polymeric material of the present disclosure may include approximately 40-80 wt % of cold water soluble polyvinyl alcohol; approximately 1-60% wt % of non-cold water soluble polyvinyl alcohol; and approximately 0-30 wt % of a propylene glycol. Formulation Table 1 below sets forth more specific blends of the polymeric materials disclosed herein and which were extruded into tubing.

FORMULATION TABLE 1

| | % Wt. of Each Ingredient | | | | |
|---|---|---|---|---|---|
| Blend # | % TC 232 | % TC 251 | % TC 253 | % TC 661 | % Propylene Glycol |
| 1 | 77.5 | 0 | 0 | 2.5 | 20 |
| 2 | 0 | 50 | 0 | 50 | 0 |
| 3 | 0 | 41.66 | 0 | 41.66 | 16.68 |
| 4 | 0 | 68.57 | 0 | 11.43 | 20 |
| 5 | 69.6 | 0 | 0 | 5.4 | 25 |
| 6 | 0 | 73 | 0 | 12 | 15 |
| 7 | 73 | 0 | 0 | 12 | 15 |
| 8 | 70 | 0 | 0 | 0 | 30 |

In one embodiment, at least a portion or component of a medical device, such as a tube made of the blends in accordance with the present disclosure may have a solubility of between about 1.0-40% mass loss in water at room temperature (RT) for 15 minutes. In another, more preferred embodiment, tubes made of the blends of the present disclosure may have a solubility of between about 2.0-25% mass loss in water at RT for 15 minutes. In determining the solubility, the following method was followed. Five (5) cm lengths of Ch 14 flushable tubing/catheters were carefully weighed and then placed in vials and immersed in water at room temperature or at 37° C. The samples were continually agitated using an Orbital shaker. Tube samples were carefully removed from the fluids at different points. In each case, the remaining fluid sample was then evaporated off and the residue of evaporation was calculated. The amount of dissolved solids was calculated as an average percentage mass loss of the sample tubes at each of the different time points. Blanks and an appropriate control were run at the same time. Separate blends of PVOH and/or PG were prepared and tested in accordance with the above-described method. The results are reported below in Table 2.

TABLE 2

| Polymer Blend (wt %/wt %) | Solubility Rate in Tube Form (Average % Mass Loss in Water @RT for 15 mins.) |
|---|---|
| TC 251/661 (50/50) | 5.4 |
| TC 251/661/PG (42/42/16) | 5.8 |
| TC 251/661/PG (69/11/20) | 7.7 |
| TC 251/661/PG (73/12/15) | 8.3 |
| TC 232/661/PG (77.5/2.5/20) | 13.6 |
| TC 232 (oven conditioned) | 17.3 |
| TC 232/661/PG (70/5/25) | 19.3 |
| TC 251/661 (50/50) | 5.4 |

In addition to being water soluble and disintegrable also possess structural properties which make them suitable for use as urinary catheters. Thus, the polymeric material made of a blend of two or more PVOH polymers in accordance with the present disclosure preferably has Young's modulus of elasticity in the range 1-100 MPa, and the flushable catheter shafts with sizes in the range Ch 6-Ch 18 made from such materials (i.e., blends) preferably have bending stiffness in the range 0.68-46835 MPa mm$^4$.

Figure 2A:
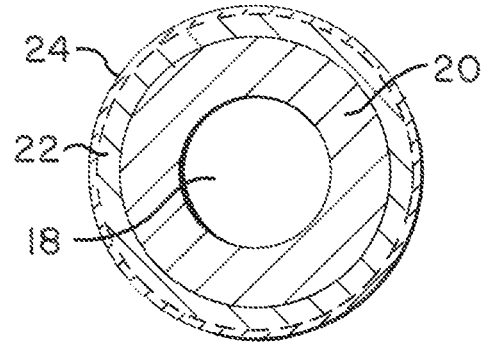
FIG. 2A is a cross-sectional view taken along 2-2 of the catheter tube of FIG. 1.

As indicated above, at least a portion of catheter shaft 12 may be made of the polymeric materials (blends) disclosed herein. With reference to FIG. 2A, catheter shaft 12 may be extruded as a tube made entirely or substantially entirely of the polymeric materials disclosed herein i.e., a blend of cold water soluble and non-cold water soluble polymers such as PVOH with or without a plasticizer such as PG. As shown in FIG. 2A, catheter tube 12, an inner (mono) layer 20 of the polymeric material. The relative amounts of the PVOH polymers that make up the blend are selected to allow for catheter tube 12 to maintain mechanical integrity during the catheterization procedure and disintegrate in water in accordance with required dissolution rates. As further shown in FIG. 2A, layer 20 also provides a substrate and support for a suitable primer layer 22 and hydrophilic top coat layer 24.

Figure 2B:
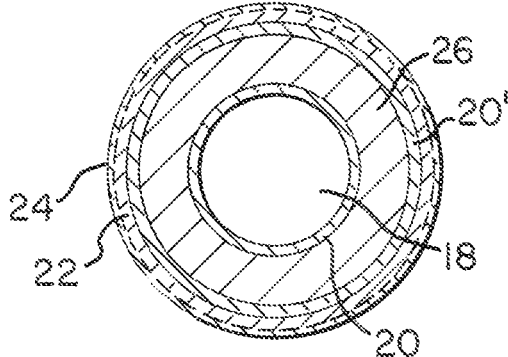
FIG. 2B is a is a cross-sectional view taken along 2-2 of an alternative embodiment of the catheter tube of FIG. 1.

FIG. 2B shows an alternative embodiment of catheter tube 12 and an alternative arrangement of utilizing the polymeric material of the present disclosure. In the embodiment of FIG. 2B, catheter tube may be (co)extruded or otherwise provided as a multi-layer tube wherein the innermost layer 20 and outermost layer 20' are made at least substantially (if not entirely) of the polymeric material (e.g., blends of cold water soluble and non-cold water soluble PVOH with or without a plasticizer such as PG). Layers 20 and 20' sandwich a middle layer 26 which may be made of a different water soluble material. In the embodiment of FIG. 2B, relative to the overall solubility of layers 20 and 20', middle layer 26 may be made of a fast-dissolving polymeric material. Layers 20 and 20' may thereby act as barriers to layer 26 and selectively control and modulate the overall disintegration of catheter tube 12. As in the embodiment of FIG. 2A, outer layer 20' which is preferably made of the polymeric material (blend) described herein may also serve as a substrate for a suitable primer layer 22 and hydrophilic top coat layer 24. In a more specific embodiment. The inner and outer layers may be made of blends of Mowiflex TC661 and/or TC161 with TC 232, TC 251 and/or TC 253 and/or propylene glycol (PG) and/or any other suitable plasticizer disclosed in U.S. Pat. No. 2,948,647 or any other plasticizer that will be known to those of skill in the art.

Thus, in accordance with the present disclosure, the bulk of the catheter shaft may be made of a monolayer or internal and/or external barrier layers as shown in FIGS. 2A and 2B. The monolayer or the outer layer is capable of providing a stable foundation for the anchorage of a hydrophilic coating, especially when in contact with a liquid activation agent that lubricates the coating and/or when the catheter is in contact with warm urine. The stable foundation, even when catheter tube 12 is exposed to liquid, prevents excessive delamination of the coating during use. Eventually, the catheter will break down in the presence of liquid but not until well after the catheterization procedure is performed and yet soon enough to meet general guide lines for flushable products. The inner and outer layers also function to modulate the dissolution rate of the bulk of the catheter during use and disposal in the toilet.

Figure 2C:
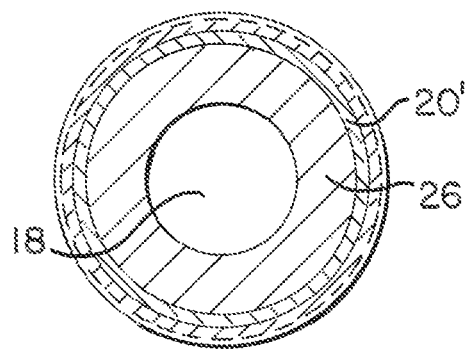
FIG. 2C is a cross-sectional view taken along 2-2 of a further alternative embodiment of the catheter tube of FIG. 1.

In FIG. 2C there is shown another alternative of catheter 10 and catheter tube 12 similar to the embodiment of FIG. 2B with the exception that an inner barrier layer 20 is not included. In FIG. 2C, layer 26 may be made of a relatively fast dissolving material. An outer layer 20' may be made of the polymeric material described herein and serves to modulate the disintegration of catheter tube 12 and acts as a substrate for a suitable primer layer 22 and hydrophilic top coat layer 24. In a more specific embodiment.

Figure 2D:
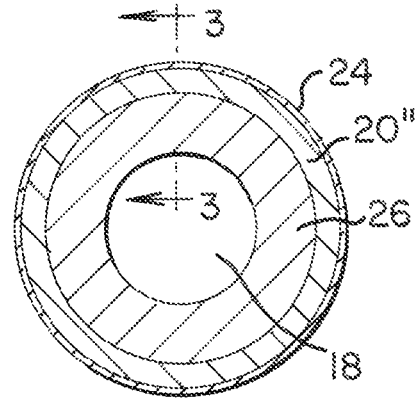
FIG. 2D is a cross-sectional view taken along 2-2 of yet another alternative embodiment of the catheter tube of FIG. 1.
Figure 3:
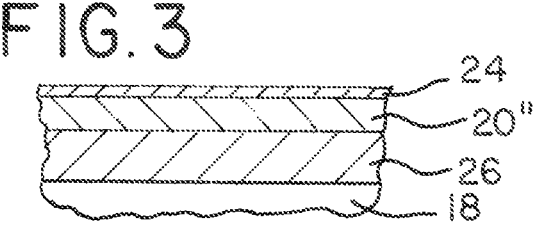
FIG. 3 is a cross-sectional view taken along 3-3 of the catheter tube of FIG. 2D.

In the embodiment of FIG. 2D, catheter tube 12 may include a relatively fast dissolving layer 26 of a polymeric material. Outer layer 20" may be the polymeric material of the present disclosure (e.g., blends of cold water soluble and non-cold water soluble PVOH with our without a plasticizer such as PG) that is further blended with another polymer such polyvinylpyrolidone (PVP). Layer 20" serves as a barrier and a primer for hydrophilic top coat 24. A longitudinal cross-sectional view is shown in FIG. 3.

Other Aspects

Aspect 1. A polymeric material comprising a blend of two or more polymers wherein one of said polymers has a first water solubility rate and another of said two or more polymers has a different water solubility rate.

Aspect 2. The polymeric material of Aspect 1 wherein said blend comprises a cold water soluble polymer and a non-cold water soluble polymer.

Aspect 3. The polymeric material of any one of Aspects 1-2 wherein said one of said two or more polymers comprises polyvinyl alcohol.

Aspect 4. The polymeric material of any one of Aspects 1-2 wherein said other of said two or more polymers comprises polyvinyl alcohol.

Aspect 5. The polymeric material of any one of Aspects 1 through 4 wherein one of said two more polymers is substantially water soluble at temperatures above 55° C.

Aspect 6. The polymeric material of any one of Aspects 1 through 5 further comprising a plasticizer.

Aspect 7. The polymeric material of any one of Aspects 1 through 5 further comprising propylene glycol.

Aspect 8. The polymeric material of any one of Aspects 1 through 7 wherein said material has a solubility rate 1.0-40% mass loss in water at room temperature for 15 minutes.

Aspect 9. The polymeric material of any one of Aspects 1 through 8 wherein said material comprising said blend has a water solubility that is different from the solubility rates of each of said one of said polymers and said other of said polymers.

Aspect 10. The polymeric material of any one of Aspects 1 through 9 comprising: a) approximately 1-80 wt % of a cold water soluble polymer; b) approximately 1-80 wt % of a non-cold water soluble polymer; and c) approximately 0-35 wt % of a plasticizer.

Aspect 11. The polymeric material of Aspect 10 wherein said cold water soluble polymer comprises polyvinyl alcohol.

Aspect 12. The polymeric material of Aspect 11 wherein said non-cold water soluble material comprises polyvinyl alcohol.

Aspect 13. The polymeric material of any one of Aspects 11-12 wherein said plasticizer comprises propylene glycol.

Aspect 14. The polymeric material of any one of Aspects 1 through 13 comprising: a) approximately 40-80 wt % of cold water soluble polyvinyl alcohol; b) approximately 30-60 wt % of non-cold water soluble polyvinyl alcohol; and c) approximately 1-30 wt % of a propylene glycol.

Aspect 15. A flushable urinary catheter comprising a shaft at least a portion of which is made of a polymeric material comprising a blend of two or more polymers wherein one of said polymers has a first water solubility rate and another of said two or more polymers has a different water solubility rate.

Aspect 16. The flushable urinary catheter of Aspect 15 wherein said blend comprises at least one cold water soluble polymer and at least one non-cold water soluble polymer.

Aspect 17. The flushable catheter of any one of Aspects 15-16 wherein said cold water soluble polymer is polyvinyl alcohol.

Aspect 18. The flushable catheter of Aspect 17 wherein said non-cold water soluble polymer is polyvinyl alcohol.

Aspect 19. The flushable catheter of any one of Aspects 15-18 wherein said material comprises: a) approximately 40-80 wt % of cold water soluble polyvinyl alcohol; b) approximately 1-60 wt % of non-cold water soluble polyvinyl alcohol; and c) approximately 0-30 wt % of a propylene glycol.

Aspect 20. The flushable catheter of any one of Aspects 15-19 wherein the size of said catheter shaft is Ch6-Ch18.

Aspect 21. The flushable catheter of any one of Aspects 15-20 wherein said shaft has a bending stiffness of approximately 0.68-46835 MPa mm4.

Aspect 22. The flushable catheter of any one of Aspects 15-21 wherein said shaft comprises a monolayer of said polymeric material coated with at least a top layer of a hydrophilic coating.

Aspect 23. The flushable catheter of any one of Aspects 15-21 wherein said shaft comprises an inner layer and an outer layer wherein one of said inner and outer layers comprises said polymeric material and the other of said inner and outer layers comprises a water soluble polymer that has a water solubility rate that is different than the water solubility rate of said polymeric material.

Aspect 24. The flushable catheter of any one of Aspects 15-21 wherein said shaft comprises an inner layer, a middle layer and an outer layer wherein at least one of said inner and outer layers comprises said polymeric material and middle said layer comprises a water soluble polymer that has a water solubility rate that is different than the water solubility rate of said polymeric material.

Aspect 25. The flushable catheter of any one of Aspects 23-24 further comprising a hydrophilic coating and an optional primer coating coated onto said outer layer.

Aspect 26. A medical device at least a portion of which comprises a polymeric material comprising a blend of two or more polymers wherein one of said polymers has a first water solubility rate and another of said at least two or more polymers has a different water solubility rate.

Aspect 27. The medical device of Aspect 26 wherein a component of said medical device comprises said polymeric material.

Aspect 28. The medical device of any one of Aspects 26-27 wherein at least said portion of said device is insertable into the body of a patient or user.

Aspect 29. The medical device of Aspect 28 wherein said at least said portion maintains a sufficient amount of mechanical strength during a time when said at least said portion is inserted into the body of the patient or user and is flushable.

It should be understood that various changes and modifications to the presently preferred embodiments and aspects described herein will be apparent to those skilled in the art. Such changes and modification can be made without departing from the spirit and scope of the invention disclosed herein.

The invention claimed is:

1. A flushable insertable medical device comprising a shaft at least a portion of which is made of a polymeric material including a blend of polyvinyl alcohol polymers, wherein the blend consists of:
   a. approximately 68 wt %-77.5 wt % of a cold-water soluble polyvinyl alcohol;
   b. approximately 2.5 wt %-11 wt % of a non-cold water-soluble polyvinyl alcohol;
   said polymeric material further including 15 wt %-25 wt % propylene glycol.

2. The medical device of claim 1 wherein the blend is selected to maintain the shape of the catheter while inserted.

3. The medical device of claim 1 wherein said shaft has a bending stiffness of approximately 0.68-46835 MPa mm$^4$.

4. The medical device of claim 1 wherein said shaft comprises an inner layer and an outer layer wherein one of said inner and outer layers comprises said polymeric material and the other of said inner and outer layers comprises a water soluble polymer that has a water solubility rate that is different than the water solubility rate of said polymeric material.

5. The medical device of claim 1 wherein said shaft comprises an inner layer, a middle layer and an outer layer wherein at least one of said inner and outer layers comprises said polymeric material and middle said layer comprises a water-soluble polymer that has a water solubility rate that is different than the water solubility rate of said polymeric material.

6. The medical device of claim 4 further comprising an optional primer coating coated onto said outer layer.

7. The medical device of claim 1, wherein the medical device comprises a urinary catheter.

* * * * *